(12) United States Patent
Fujii et al.

(10) Patent No.: US 6,281,379 B1
(45) Date of Patent: Aug. 28, 2001

(54) PROCESS FOR PRODUCING NORSTATIN DERIVATIVES

(75) Inventors: Akio Fujii; Masanobu Sugawara; Kenji Inoue, all of Hyogo (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/578,446

(22) Filed: May 26, 2000

(30) Foreign Application Priority Data

May 28, 1999 (JP) .................................... 11-149272
Jan. 7, 2000 (JP) .................................... 12-001706

(51) Int. Cl.$^7$ ........................ C07C 229/00; C07C 321/00
(52) U.S. Cl. ........................... 560/39; 560/170; 562/444; 562/567; 564/340
(58) Field of Search .................... 560/39, 170; 562/444, 562/567; 564/340

(56) References Cited

U.S. PATENT DOCUMENTS 5,442,105 * 8/1995 Sayo et al. .
5,817,859 * 10/1998 Suzuki et al. .
6,020,518 * 2/2000 Matsumoto et al. .

FOREIGN PATENT DOCUMENTS

| 0341 462 | 11/1989 | (EP) | ............................. C07C/99/00 |
| 08259519 | 10/1996 | (EP) | ............................ C07C/317/28 |
| 0767 168 A2 | 4/1997 | (EP) | ............................ C07C/327/30 |

* cited by examiner

*Primary Examiner*—Paul J. Killos
*Assistant Examiner*—Mahreen Chaudhry
(74) *Attorney, Agent, or Firm*—Sughrue, Mion, Zinn, Macpeak & Seas, PLLC

(57) ABSTRACT

This invention to provide a process for producing an optically active threo-phenylnorstatin derivative which does not require a toxic cyanating agent or a costly reagent, or a complicated procedure, and can be practiced on a commercial scale.

This invention is directed to a process for producing a β-amino-α-hydroxy acid derivative which comprises treating either a γ-amino-β-keto sulfoxide derivative with a halogenating agent to produce a γ-amino-α-halo-β-keto sulfoxide derivative, treating the same with an acid and an alcohol to produce a β-amino-α-keto ester derivative or β-amino-α-keto acid derivative, and followed by reducing.

38 Claims, No Drawings

PROCESS FOR PRODUCING NORSTATIN DERIVATIVES

FIELD OF THE INVENTION

The present invention relates to a process for producing a β-amino-α-hydroxy acid derivative of use as an intermediate in the production of pharmaceuticals and agrochemicals, particularly an optically active threo-phenylnorstatin derivative, and to a process for producing a β-amino-α-keto ester derivative or a γ-amino-α-halo-β-keto sulfoxide derivative of use as an intermediate thereof.

PRIOR ART

The hitherto-known technology for producing an optically active threo-phenylnorstatin derivative includes:

(1) the process in which an N-protected aldehyde derivative of phenylalanine is treated with a silyl cyanide and the resulting cyanohydrin compound is hydrolyzed (Japanese Kokai Publication Hei-2-28144);

(2) the process in which an N-protected aldehyde derivative of phenylalanine is cyanated in the presence of a phase transfer catalyst and acetic anhydride (Japanese Kokai Publication Hei-2-56547);

(3) the process in which an N-protected aldehyde derivative of phenylalanine is cyanated to a cyanohydrin derivative, followed by being subjected to isomerization-crystallization in the presence of an amine (Japanese Kokai Publication Hei-9-27834);

(4) the process which comprises converting N-phthaloyl-protected phenylalanine to an acid chloride, reacting it with a silyl cyanide to give a cyanoketone, converting it to a keto ester, and reducing the same with zinc borohydride or the like (EP-553343);

(5) the multi-step process utilizing an optically active 3,4-butenediol wherein a phenylnorstatin derivative is synthesized through an aziridine derivative and an oxazolidone derivative [Bioorg. Med. Chem. Lett. (1995), 5 (24), 2959]; and (6) the process in which an N-protected α-aminoacetophenone derivative is reacted with glyoxylic acid and the reaction product is subjected to optical resolution, crystallization and catalytic reduction (Japanese Kokai Publication Sho-55-79353).

However, the processes (1) through (4) invariably require the use of a cyanating agent which is highly toxic and calls for meticulous care in handling, while the process (5) involves many steps and requires costly reagents. The process (6) requires a complicated procedure for isolating the desired optically active threo-compound from a mixture of 4 different isomers. Thus, any of the known processes has some disadvantages or others to be overcome for exploitation as an industrially profitable method for production of optically active threo-norstatin derivatives.

SUMMARY OF THE INVENTION

In view of the above state of the art, the present invention has for its object to provide a process for producing an optically active threo-phenylnorstatin derivative which does not require a toxic cyanating agent or a costly reagent, or a complicated procedure, and can be practiced on a commercial scale.

Under the circumstances the inventors of the present invention explored enthusiastically for a production technology by which an optically active threo-norstatin derivative, particularly an optically active threo-phenylnorstatin derivative, may be produced efficiently from an optically active amino acid ester derivative which is readily available, particularly an optically active phenylalanine derivative, as an starting material. As a result, they discovered a process by which a β-amino-α-hydroxy acid derivative, particularly an optically active threo-phenylnorstatin derivative and an intermediate thereof, can be produced with good efficiency from an amino acid ester derivative, particularly an optically active phenylalanine ester.

The present invention, therefore, is directed to a process for producing a β-amino-α-hydroxy acid derivative which comprises treating either a γ-amino-β-keto sulfoxide derivative of the formula (1);

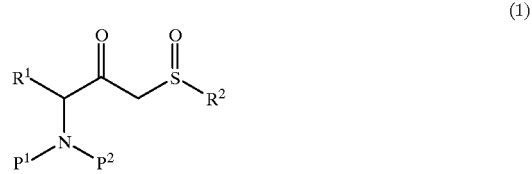

(1)

wherein $R^1$ represents a substituted or unsubstituted alkyl group of 1 to 20 carbon atoms, a substituted or unsubstituted aralkyl group of 7 to 30 carbon atoms or a substituted or unsubstituted aryl group of 6 to 30 carbon atoms; $R^2$ represents a substituted or unsubstituted alkyl group of 1 to 10 carbon atoms, a substituted or unsubstituted aralkyl group of 7 to 20 carbon atoms or a substituted or unsubstituted aryl group of 6 to 20 carbon atoms; $P^1$ and $P^2$ may be the same or different and each represents a substituted or unsubstituted benzyl group, or a γ-amino-β-keto sulfoxide derivative metal salt of the formula (6);

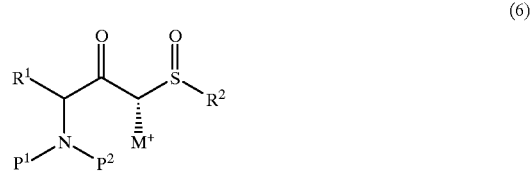

(6)

wherein $R^1$, $R^2$, $P^1$ and $P^2$ are as defined above; M represents an alkali metal or an alkaline earth metal halide, with a halogenating agent to produce a γ-amino-α-halo-β-keto sulfoxide derivative of the formula (2);

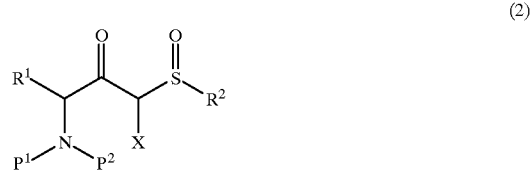

(2)

wherein $R^1$, $R^2$, $P^1$ and $P^2$ are as defined above; X represents a halogen atom, treating the derivative (2) with an acid and an alcohol of the formula (3);

$R^3OH$ (3)

wherein $R^3$ represents a substituted or unsubstituted alkyl group of 1 to 10 carbon atoms or a substituted or unsubstituted aralkyl group of 7 to 20 carbon atoms, to produce a β-amino-α-keto ester derivative or β-amino-α-keto acid derivative of the formula (4);

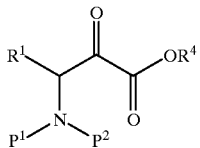

(4)

wherein $R^1$, $P^1$ and $P^2$ are respectively as defined above; $R^4$ represents a hydrogen atom, or a substituted or unsubstituted alkyl group of 1 to 10 carbon atoms or substituted or unsubstituted aralkyl group of 7 to 20 carbon atoms which corresponds to $R^3$ in the above formula (3), and reducing the same derivative (4), optionally followed by cleaving the ester and/or deprotecting the amino group to give a β-amino-α-hydroxy acid derivative of the formula (5);

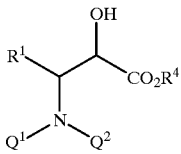

(5)

wherein $R^1$ and $R^4$ are respectively as defined above; $Q^1$ represents a hydrogen atom, or a substituted or unsubstituted benzyl group corresponding to $P^1$ in the above formula (1); $Q^2$ represents a hydrogen atom, or a substituted or unsubstituted benzyl group corresponding to $P^2$ in the above formula (1).

The present invention is further directed to a process for producing a β-amino-α-keto ester derivative or β-amino-α-keto acid derivative of the above formula (4)

which comprises treating a γ-amino-β-keto sulfoxide derivative of the above formula (1) or γ-amino-β-keto sulfoxide derivative of the above formula (6) with a halogenating agent to produce a γ-amino-α-halo-β-keto sulfoxide derivative of the above formula (2) and treating the derivative (2) with an acid and an alcohol of the above formula (3).

The present invention is further directed to a process for producing a γ-amino-α-halo-β-keto sulfoxide derivative of the above formula (2)

which comprises treating a γ-amino-β-keto sulfoxide derivative of the above formula (1) or a γ-amino-β-keto sulfoxide derivative metal salt of the above formula (6) with a halogenating agent.

The present invention is further directed to a compound of the above formula (2).

The present invention is now described in detail.

DETAILED DESCRIPTION OF THE INVENTION

Referring to the γ-amino-β-keto sulfoxide derivative of the formula (1), $R^1$ represents a substituted or unsubstituted alkyl group of 1 to 20 carbon atoms, a substituted or unsubstituted aralkyl group of 7 to 30 carbon atoms or a substituted or unsubstituted aryl group of 6 to 30 carbon atoms.

The substituted or unsubstituted alkyl group of 1 to 20 carbon atoms is not particularly restricted but includes methyl, ethyl, isopropyl, isobutyl, t-butyl, hydroxymethyl, 1-hydroxyethyl, mercaptomethyl and methylthiomethyl, among others.

The substituted or unsubstituted aralkyl group of 7 to 30 carbon atoms is not particularly restricted, either, but includes benzyl, p-hydroxybenzyl, p-methoxybenzyl, p-chlorobenzyl, phenylthiomethyl and α-phenethyl, among others.

The substituted or unsubstituted aryl group of 6 to 30 carbon atoms is not particularly restricted but includes phenyl, p-hydroxyphenyl and p-methoxyphenyl, among others.

$R^1$ above represents the side chain of an ordinary α-amino acid or the side chain of an α-amino acid derivative produced by derivatizing such an ordinary α-amino acid, and insofar as it is a substituted or unsubstituted alkyl group of 1 to 20 carbon atoms, a substituted or unsubstituted aralkyl group of 7 to 30 carbon atoms or a substituted or unsubstituted aryl group of 6 to 30 carbon atoms, it is not particularly restricted, although $R^1$ is preferably benzyl.

Referring to the above γ-amino-γ-keto sulfoxide derivative of the formula (1), $R^2$ represents a substituted or unsubstituted alkyl group, such as methyl, ethyl, isopropyl, butyl, isobutyl and the like, a substituted or unsubstituted aralkyl group of 7 to 20 carbon atoms, such as benzyl, p-methoxybenzyl, β-phenethyl and the like, or a substituted or unsubstituted aryl group of 6 to 20 carbon atoms, such as phenyl, p-methoxyphenyl and the like. Preferably, $R^2$ is methyl.

$P^1$ and $P^2$ each is an amino-protecting group. $P^1$ and $P^2$ may be the same or different and each represents a substituted or unsubstituted benzyl group such as benzyl, p-methoxybenzyl and the like. Preferred is benzyl.

Referring to the above γ-amino-β-keto sulfoxide derivative of the formula (6), $R^1$, $R^2$, $P^1$ and $P^2$ are as defined in the above formula (1). M represents an alkali metal or an alkaline earth metal halide, including sodium, potassium, lithium, chloro magnesium, bromo magnesium and so on.

Referring to the above γ-amino-α-halo-β-keto sulfoxide derivative of the formula (2), $R^1$, $R^2$, $P^1$ and $P^2$ are as defined in the above formula (1). X represents a halogen atom such as chloro, bromo, iodo or fluoro. Preferred is chloro or bromo and the more preferred is chloro.

Referring to the above alcohol of the formula (3), $R^3$ represents a substituted or unsubstituted alkyl group of 1 to 10 carbon atoms, such as methyl, ethyl, n-propyl, isopropyl, n-butyl, isobutyl and the like, or a substituted or unsubstituted aralkyl group of 7 to 20 carbon atoms, such as benzyl, p-methoxybenzyl and the like. Preferred is methyl or ethyl.

The above alcohol of the formula (3) specifically includes methyl alcohol, ethyl alcohol, n-propyl alcohol, isopropyl alcohol, n-butyl alcohol, isobutyl alcohol and benzyl alcohol, among others. Preferred is methyl alcohol or ethyl alcohol.

Referring to the above β-amino-α-keto ester derivative of the formula (4), $R^1$, $P^1$ and $P^2$ are as defined in the above formula (2). $R^4$ represents a hydrogen atom, or the same group as $R^3$ in the above formula (3). Preferably, $R^4$ is the same as $R^3$.

Referring to the above β-amino-α-hydroxy acid derivative of the formula (5), $R^1$ and $R^4$ are as defined in the above formulas (2) and (4), respectively. $Q^1$ represents a hydrogen atom, or the same group as $P^1$ in the above formula (1). $Q^2$ represents a hydrogen atom, or the same group as $P^2$ in the above formula (1).

In the present invention, a γ-amino-β-keto sulfoxide derivative of the formula (1) or a γ-amino-β-keto sulfoxide derivative metal salt of the formula (6) is used as the starting compound.

The production of the compound of the formula (1) is now explained. The γ-amino-β-keto sulfoxide derivative of the formula (1) can be produced by, for example, reacting an α-amino acid ester derivative of the formula (7);

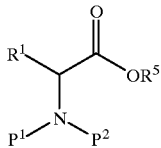 (7)

(wherein $R^1$ $P^1$ and $P^2$ are respectively as defined in the above formula (1); $R^5$ represents a substituted or unsubstituted alkyl group of 1 to 10 carbon atoms, a substituted or unsubstituted aralkyl group of 7 to 20 carbon atoms or a substituted or unsubstituted aryl group of 6 to 20 carbon atoms) with a sulfoxide metal salt of the formula (8);

 (8)

(wherein $R^2$ is the same as the above formula (2); M represents an alkali metal or an alkaline earth metal halide) in accordance with the procedure described in Japanese Kokai Publication Hei-8-259519 or any same procedure as the procedure described in Japanese Kokai Publication Hei-8-259519.

Referring to the above α-amino acid ester derivative of the formula (7), $R^1$ is the same as $R^1$ in the formula (1). $R^5$ may for example be methyl, ethyl, n-propyl, isopropyl, n-butyl, isobutyl, benzyl and the like. Preferred is benzyl, methyl or ethyl.

Referring to the above sulfoxide metal salt of the formula (8), M represents an alkali metal or an alkaline earth metal halide, including sodium, potassium, lithium, chloro magnesium, bromo magnesium and so on.

The above sulfoxide metal salt of the formula (8) can be typically prepared by reacting a sulfoxide compound, such as dimethyl sulfoxide, methylphenyl sulfoxide and the like, with a base. For use in the contemplated reaction, said salt may be prepared in advance or caused to form in the course of the reaction. Said bases include sodium hydride, sodium amide, sodium t-butoxide, sodium ethoxide, sodium methoxide, potassium hydride, potassium amide, potassium t-butoxide, lithium hydride, lithium amide, n-butyllithium, lithium diisopropylamide, bromo magnesium diisopropylamide, chloro magnesium diisopropylamide, t-butylmagnesium chloride, t-butylmagnesium bromide and magnesium ethoxide, among others.

The solvent for use in preparing the sulfoxide metal salt includes tetrahydrofuran, t-butyl methyl ether, diethyl ether, 1,2-dimethoxyethane, N,N-dimethylformamide, N-methylpyrrolidone, 1,3-dimethylimidazolidinone, toluene, benzene, and so on. Sulfoxides such as dimethyl sulfoxide can also be used as the solvent or used in admixture with any of the above-mentioned solvents.

The reaction conditions for use in the preparation of said sulfoxide metal salt or in the reaction thereof with the amino acid ester derivative of the formula (7) vary with the kind of base used but a typical procedure may comprise treating said sulfoxide with the base in said solvent at, for example, −50° C. to 90° C. with stirring for about 30 minutes to about 5 hours to prepare the sulfoxide metal salt and, then, reacting it with said N-protected α-amino acid ester derivative of the formula (7).

The after-treatment following the reaction can be typically carried out by adding an acidic aqueous solution such as diluted hydrochloric acid, ammonium chloride thereof, etc. to the reaction mixture or adding the reaction mixture to such an acidic solution and carrying out the routine extraction, washing and concentration procedure, for instance. The mixture of diastereomers which forms may be optionally isolated and purified by column chromatography or the like or directly used in accordance with the present invention.

Now, the process for producing said γ-amino-α-halo-β-keto sulfoxide derivative of the formula (2) by reacting said γ-amino-β-keto sulfoxide derivative of the formula (1) with said halogenating agent is now described.

The halogenating agent is not particularly restricted only if it has halogenating capacity, thus including sulfuryl chloride, N-chlorosuccinimide (NCS), N-bromosuccinimide (NBS), 1,3-dibromo-5,5-dimethylhydantoin, bromine, chlorine, hexachloroacetone, iron chloride and so on. Preferred from economic and reactivity points of view are sulfuryl chloride, N-bromosuccinimide (NBS), 1,3-dibromo-5,5-dimethylhydantoin and bromine. The more preferred is N-bromosuccinimide (NBS) or 1,3-dibromo-5,5-dimethylhydantoin.

The amount of said halogenating agent is dependent on the kind and halogenating capacity per mole of the halogenating agent. Taking sulfuryl chloride or N-bromosuccinimide as an example, the halogenating agent can be used in a proportion of preferably 0.5 to 20 molar equivalents, more preferably 0.5 to 5 molar equivalents, with respect to the compound of the formula (1).

The reaction solvent includes dichloromethane, chloroform, toluene, benzene, tetrahydrofuran, diethyl ether, diisopropyl ether, t-butyl dimethyl ether, N,N-dimethylformamide, N-methylpyrrolidone, acetone, methyl ethyl ketone, methyl alcohol and ethyl alcohol, among others.

The halogenation reaction can be carried out by, for example, treating the compound of the formula (1) with the halogenating agent in said solvent preferably at a temperature of −78° C. to 80° C., preferably with stirring, for about 5 minutes to about 20 hours.

The production of said γ-amino-β-keto sulfoxide derivative metal salt of the formula (6) is now described in detail.

This compound can be prepared in advance by treating a γ-amino-β-keto sulfoxide derivative of the formula (1) with a base. The base mentioned just above includes sodium hydride, sodium amide, sodium t-butoxide, sodium ethoxide, sodium methoxide, potassium hydride, potassium amide, potassium t-butoxide, lithium hydride, lithium amide, n-butyllithium, lithium diisopropylamide, bromo magnesium diisopropylamide, chloro magnesium diisopropylamide, t-butylmagnesium chloride, t-butylmagnesium bromide and magnesium ethoxide, among others. The resulting γ-amino-β-keto sulfoxide derivative metal salt of the formula (6) is preferably submitted to said halogenation reaction in the form of the reaction mixture as such.

Moreover, the γ-amino-β-keto sulfoxide derivative metal salt of the formula (6) can be prepared by reacting an α-amino acid ester derivative of the formula (7) with a sulfoxide metal salt of the formula (8) in the manner described hereinbefore. In order to obtain a γ-amino-β-keto sulfoxide derivative of the formula (1), the reaction product of the compounds (7) and (8) is hydrolyzed by adding an acidic aqueous solution to the reaction mixture but, if desired, the γ-amino-β-keto sulfoxide derivative metal salt of the formula (6) as such may be submitted to the next halogenation reaction omitting the hydrolysis step.

The step of reacting said γ-amino-β-keto sulfoxide derivative metal salt of the formula (6) with said halogenating agent to produce said γ-amino-α-halo-β-keto sulfoxide derivative of the formula (2) can be carried out in the same manner as the production of said γ-amino-β-keto sulfoxide derivative of the formula (1) but the objective γ-amino-α-monohalo-β-keto sulfoxide derivative can be produced with high selectivity by using N-bromosuccinimide (NBS), 1,3-dibromo-5,5-dimethylhydantoin or bromine, more preferably N-bromosuccinimide (NBS), as the halogenating agent.

The after-treatment following the halogenation reaction may for example comprise neutralizing the reaction mixture with an aqueous solution of sodium hydrogencarbonate and carrying out the routine extraction, washing and concentration procedure. The γ-amino-α-halo-β-keto sulfoxide derivative of the formula (2) can be isolated by the routine fractional purification method such as column chromatography. However, the crude product as such may be submitted to the next reaction step omitting such purification or even the halogenation reaction mixture may be directly submitted to the next step.

The γ-amino-α-halo-β-keto sulfoxide derivative of the formula (2) as produced by the above reaction is a novel compound. When this reaction is carried out using an optically active form of the compound (1), the optically active form of the compound (2) can be advantageously obtained without being compromised in optical purity.

The step of treating said γ-amino-α-halo-β-keto sulfoxide derivative of the formula (2) with said acid and said alcohol of the formula (3) to prepare said β-amino-α-keto ester derivative or β-amino-α-keto acid derivative of the formula (4) is now described in detail.

This reaction can be typically carried out by treating said γ-amino-α-halo-β-keto sulfoxide derivative of the formula (2) with an acid in said alcohol of the formula (3) or treating the derivative (2) with an acid in a solvent in the presence of said alcohol of the formula (3).

The acid includes hydrochloric acid, sulfuric acid, p-toluenesulfonic acid, camphorsulfonic acid, methanesulfonic acid, acetic acid, trifluoroacetic acid and trifluoromethanesulfonic acid, among others. Acidic ion exchange resins such as Nafion-H may also be used likewise.

The solvent mentioned above includes dichloromethane, chloroform, toluene, benzene, tetrahydrofuran, diethyl ether, diisopropyl ether, t-butyl dimethyl ether, N,N-dimethylformamide, N-methylpyrrolidone, acetone, methyl ethyl ketone, and so on.

This reaction can be typically carried out by treating said γ-amino-α-halo-β-keto sulfoxide derivative of the formula (2) with said acid and said alcohol of the formula (3), optionally in the presence of a solvent other than said alcohol, preferably at a temperature of −70° C. to 100° C., preferably for 10 minutes to 20 hours, more preferably 30 minutes to 10 hours.

By this reaction, the β-amino-α-keto ester derivative is chiefly produced.

When the reaction mixture obtained in the preceding step is used as it is in this reaction step, the halogenation reaction mixture, for instance, can be treated in the same manner as above.

In this connection, when an optically active compound is used as the compound of the formula (1), the optically active compound of the formula (4) can be advantageously obtained without being compromised in optical purity.

The step of producing a β-amino-α-hydroxy ester derivative of the formula (5) wherein $Q^1=P^1$, $Q^2=P^2$ and $R^4=R^3$ by reducing the β-amino-α-keto ester derivative of the formula (4) is now described in detail.

The reduction method is not particularly restricted but includes, among others, the reduction process using a metal hydride such as sodium borohydride, lithium borohydride, potassium borohydride, zinc borohydride, diisobutylaluminum hydride and the like, the reduction process using a silane reducing agent such as diphenylsilane, diethylsilane, trimethoxysilane, trichlorosilane and the like, the MPV reduction process using aluminum triisopropoxide, aluminum sec-butoxide or the like, and the catalytic reduction process using a metal catalyst such as Pd, Pt, Rh, Ru and the like. Preferred is the reduction process using a metal hydride. The conditions of these reduction reactions may be those well known in the art.

Among the β-amino-α-hydroxy ester derivatives of the formula (5) which are produced on reduction of β-amino-α-keto ester derivatives of the formula (4), the compound wherein $Q^1=P^1$, $Q^2=P^2$ and $R^4=R^3$ occurs as threo and erythro isomers, and the diastereomer ratio is dependent on the species of $R^1$ in formula (4) or the reduction process used. This reduction reaction is preferably conducted stereoselectively, and the compound of the formula (5) is preferably the threo-isomer. Specifically, the threo-isomer can be obtained with high selectivity by carrying out the reduction reaction using sodium borohydride, for instance, as the reducing agent.

Referring to the above β-amino-α-hydroxy ester derivative of the formula (5), the compound wherein $Q^1=P^1$, $Q^2=P^2$ and $R^4=R^3$ is optionally subjected to ester cleavage and amino-deprotection to give the compound of the formula (5) wherein each of $Q^1$, $Q^2$ and $R^4$ is a hydrogen atom. It is also possible to carry out only the ester cleavage reaction to give the compound of the formula (5.) wherein $Q^1=P^1$, $Q^2=P^2$ and $R^4=H$ or carry out only the amino-deprotection reaction to give the compound wherein $Q^1=H$, $Q^2=H$ and $R^4=R^3$. In this connection, when the β-amino-α-keto acid derivative is used as the compound of the formula (4), the compound of the formula (5) wherein $Q^1=P^1$, $Q^2=P^2$ and $R^4=H$ can be obtained without carrying out the ester cleavage reaction, or the compound wherein each of $Q^1$, $Q^2$ and $R^4$ is a hydrogen atom by carrying out only the amino-deprotection reaction.

When both the ester cleavage and amino deprotection reactions are to be carried out, the two reactions may be simultaneously carried out in one operation (for example, the catalytic reduction process described below) or carried out independently. In the latter case, the ester cleavage reaction may either precede or follow the amino deprotection reaction.

The method for said ester cleavage is not particularly restricted but the various processes known to a person skilled in the art can be judiciously employed. For example, the hydrolysis reaction using an ordinary acid or base can be used and for cleavage of the benzyl ester, the conventional catalytic reduction process can be utilized.

The method for said amino deprotection is not particularly restricted but the various processes known to a person skilled in the art can be judiciously employed. For example, the catalytic reduction method used routinely for hydrogenolysis of a benzyl ester can be utilized. The metal catalyst for use in this process includes palladium, platinum and nickel, which are conventionally used for elimination of the N-dibenzyl group.

In the process according to the present invention, the optically active compound of the formula (5) can be advantageously obtained without being compromised in optical purity by using an optically active compound as the compound of the formula (1). It is particularly desirable that optically active threo derivatives be provided.

In accordance with the present invention described above, β-amino-α-hydroxy acid derivatives, particularly threo-phenylnorstatin derivatives, can be produced from α-amino acids such as phenylalanine with advantage on a commercial scale, and when optically active α-amino acids are used, optically active threo-phenylnorstatin derivatives can be obtained.

BEST MODE FOR CARRYING OUT THE INVENTION

The following examples are intended to illustrate the present invention in further detail and should by no means be construed as defining the scope of the invention.

EXAMPLE 1

Production of (3S)-3-N,N-dibenzylamino-2-oxo-4-phenylbutyric acid methyl ester

A solution of (3S)-3-N,N-dibenzylamino-1-methylsulfinyl-2-oxo-4-phenylbutane (diastereomer ratio; 60:40, optical purities; 95% ee & 92% ee, respectively, 405 mg, 1.0 mmol) in methylene chloride (2 mL) was cooled to −78° C. and sulfuryl chloride (0.08 mL, 1.0 mmol) was added dropwise. After 30 minutes of stirring, methanol (2 mL) and concentrated hydrochloric acid (0.1 mL) were added. The mixture was then heated and stirred at 40° C. for 5 hours. After the reaction system was cooled to room temperature, the mixture was diluted with an aqueous solution of sodium hydrogencarbonate and extracted with ethyl acetate. The organic layer was extracted with water and saturated NaCl solution and the extract was dehydrated over anhydrous sodium sulfate, filtered, and concentrated. The residue was purified by silica gel chromatography (hexane:ethyl acetate=15:1) to provide 130 mg of (3S)-3-N,N-dibenzylamino-2-oxo-4-phenylbutyric acid methyl ester as light-yellow oil. Yield: 33%. The optical purity of this product as determined by HPLC analysis using a chiral column was 83% ee.

$^1$H-NMR (400 MHz, CDCl$_3$) δ: 2.94 (dd, J=4.4, 13.7 Hz, 1H), 3.15 (dd, J=8.8, 13.7 Hz, 1H), 3.58 (d, J=13.5 Hz, 2H), 3.70 (s, 3H), 3.78 (d, J=13.5 Hz, 2H), 4.29 (dd, J=4.4, 8.8 Hz, 1H), 7.14–7.33 (m, 15H).

HPLC conditions: Column: DAICEL CHIRALCEL OD (250 mm×4.6 mm); Mobile phase: hexane/2-propanol=99/1; Flow rate: 0.8 ml/min; Temperature: 30° C. Retention times: 20.8 min (S), 24.1 min (R).

EXAMPLE 2

Production of 3R)-3-N,N-dibenzylamino-2-oxo-4-phenylbutyric Acid Methyl Ester

A solution of (3R)-3-N,N-dibenzylamino-1-methylsulfinyl-2-oxo-4-phenylbutane (diastereomer ratio; 55:45, optical purities; 97% ee & 98% ee, respectively, 405 mg, 1.0 mmol) in methylene chloride (2 mL) was cooled to −78° C. and sulfuryl chloride (0.08 mL, 1.0 mmol) was added dropwise. After 30 minutes of stirring, methanol (2 mL) and concentrated hydrochloric acid (0.1 mL) were added, and the mixture was heated and stirred at 40° C. for 3 hours. After the reaction system was cooled to room temperature, the mixture was extracted with an aqueous solution of sodium hydrogencarbonate and ethyl acetate. The organic layer was extracted with water and saturated NaCl solution and the extract was dehydrated over anhydrous sodium sulfate, filtered, and concentrated. The residue was purified by silica gel chromatography (hexane:ethyl acetate=15:1) to provide 96 mg of (3R)-3-N,N-dibenzylamino-2-oxo-4-phenylbutyric acid methyl ester. Yield 25%. The $^1$H-NMR spectrum of this compound was identical with that of the compound obtained in Example 1. The optical purity of this product as determined by HPLC analysis using a chiral column was 93% ee.

EXAMPLE 3

Production of (3S)-1-chloro-3-N,N-dibenzylamino-1-methylsulfinyl-2-oxo-4-phenylbutane A solution of (3S)-3-N,N-dibenzylamino-1-methylsulfinyl-2-oxo-4-phenylbutane (diastereomer ratio; 60:40, optical purities; 95% ee & 92% ee, respectively, 405 mg, 1.0 mmol) in methylene chloride (2 mL) was cooled to −78° C. and sulfuryl chloride (0.08 mL, 1.0 mmol) was added dropwise. After 5 minutes, an aqueous solution of sodium hydrogencarbonate was added and, at room temperature, the reaction mixture was extracted with ethyl acetate. The extract was washed with water and saturated NaCl solution, dehydrated over anhydrous sodium sulfate, and concentrated. The residue was purified by silica gel chromatography (hexane:ethyl acetate=5:1) to provide 290 mg of a mixture of diastereomers of (3S)-1-chloro-3-N,N-dibenzylamino-1-methylsulfinyl-2-oxo-4-phenylbutane as yellow oil. Yield: 66%.

$^1$H-NMR (400 MHz, CDCl$_3$) δ: 1.75 (s, 2.1H), 1.85 (s, 0.9 H), 3.03–3.24 (m, 2H), 3.51–3.61 (m, 2H), 3.80–4.10 (m, 3H), 5.64 (s, 0.7H), 5.84 (s, 0.3H), 7.11–7.42 (m, 15H).

EXAMPLE 4

Production of (3S)-3-N,N-dibenzylamino-2-oxo-4-phenylbutyric Acid Methyl Ester

A solution of (3S)-3-N,N-dibenzylamino-1-methylsulfinyl-2-oxo-4-phenylbutane (diastereomer ratio; 60:40, optical purities; 95% ee & 92% ee, respectively, 620 mg, 1.53 mmol) in methylene chloride (3 mL) was cooled to −78° C. and sulfuryl chloride (0.12 mL, 1.53 mmol) was added dropwise. After 5 minutes, an aqueous solution of sodium hydrogencarbonate was added and, at room temperature, the reaction mixture was extracted with ethyl acetate. The extract was washed with water and saturated NaCl solution, dehydrated over anhydrous sodium sulfate, and concentrated. The resulting mixture of diastereomers of (3S)-1-chloro-3-N,N-dibenzylamino-1-methylsulfinyl-2-oxo-4-phenylbutane was not purified but dissolved in methanol (5 mL), and after addition of concentrated hydrochloric acid (0.1 mL), the solution was refluxed for 6 hours. After cooling to room temperature, the reaction mixture was neutralized with an aqueous solution of sodium hydrogencarbonate, concentrated, and extracted with ethyl acetate and water. The organic layer was washed with water and saturated NaCl solution, dehydrated over anhydrous sodium sulfate, filtered and concentrated. The residue was purified by silica gel chromatography (hexane:ethyl acetate= 20:1) to provide 160 mg of (3S)-3-N,N-dibenzylamino-2-oxo-4-phenylbutyric methyl ester. Yield: 27%. The $^1$H-NMR spectrum of this compound was identical with that of the compound obtained in Example 1. The optical purity of this product as determined by HPLC analysis using a chiral column was 90% ee.

EXAMPLE 5

Production of (2R, 3S)-3-N,N-dibenzylamino-2-hydroxy-4-phenylbutyric Acid Methyl Ester A solution of (3S)-3-N,N-dibenzylamino-2-oxo-4-phenylbutyric acid methyl ester (79 mg, 0.20 mmol) in methanol (2 mL) was cooled to 0° C. and sodium borohydride (11 mg, 0.30 mmol) was then added. After one hour, the reaction was stopped with diluted hydrochloric acid and the reaction mixture was extracted with ethyl acetate. The extract was washed with water and saturated NaCl solution, dehydrated over anhydrous sodium sulfate, filtered, and concentrated. The residue was purified by thin-layer chromatography (hexane:ethyl acetate=2:1) to provide 63 mg of (2R, 3S)-3-N,N-dibenzylamino-2-hydroxy-4-phenylbutyric acid methyl ester as colorless oil. Yield: 82%.

$^1$H-NMR (400 MHz, CDCl$_3$) δ: 3.09–3.23 (m, 3H), 3.40 (s, 3H), 3.45 (d, 13.2 Hz, 2H), 4.00 (d, J=3.9 Hz, 1H), 4.12 (d, J=13.2 Hz, 2H), 7.20–7.33 (m, 15H).

EXAMPLE 6

Production of (3S)-3-N,N-dibenzylamino-2-oxo-4-phenylbutyric Acid Methyl Ester

Sodium hydride (60%, 0.5 g, 12.5 mmol) was suspended in DMSO (5.3 mL, 75 mmol) and tetrahydrofuran (5 mL) and the suspension was heated at 60° C. for 2 hours. The resulting solution was cooled to 0° C. and a solution of N,N-dibenzylphenylalanine benzyl ester (2.29 g, chemical purity: 89%, 4.7 mmol) in tetrahydrofuran (5 mL) was added dropwise. After one hour, a solution of N-bromosuccinimide (1.1 g, 6 mmol) in tetrahydrofuran (10 mL) was added dropwise and the reaction was further carried out for 1 hour. This reaction mixture was added to 20 ml of 1 N-hydrochloric acid and extracted with ethyl acetate (50 mL×3). The organic layer was washed with aqueous sodium hydrogencarbonate solution, water, and saturated NaCl solution (50 mL each), dehydrated over anhydrous sodium sulfate, filtered, and concentrated to provide crude (3S)-1-bromo-3-N,N-dibenzylamino-1-methylsulfinyl-2-oxo-4-phenylbutane. To this concentrate, 20 mL of methanol and 0.1 mL of concentrated hydrochloric acid were added and the reaction was carried out at 70° C. for 3 hours. After cooling to room temperature, the reaction mixture was neutralized with an aqueous solution of sodium hydrogencarbonate and concentrated, and the methanol was then distilled off. The residue was diluted with ethyl acetate (50 mL) and water (50 mL) and, after phase separation, the aqueous layer was extracted with ethyl acetate (50 mL). The organic layer was washed with saturated NaCl solution, dehydrated over anhydrous sodium sulfate, and concentrated. The crude product thus obtained was purified by silica gel column chromatography (hexane: ethyl acetate= 10:1) to provide 1.11 g of (3S)-3-N,N-dibenzylamino-2-oxo-4-phenylbutyricacid methyl ester. Yield: 61%. The $^1$H-NMR of this compound was identical with that of the compound obtained in Example 1.

EXAMPLE 7

Production of (2R, 3S)-3-N,N-dibenzylamino-2-hydroxy-4-phenylbutyric Acid Methyl Ester A methanolic solution of sodium borohydride (566 mg, 14.9 mmol) was cooled to 0° C. and a solution of (3S)-3-N,N-dibenzylamino-2-oxo-4-phenylbutyric acid methyl ester (3.87 g, 10.0 mmol) in methanol (30 mL) was added dropwise over 35 minutes. The mixture was further stirred for 3 hours. The reaction was then stopped with 30 mL of 1 N-hydrochloric acid and the methanol was distilled off under reduced pressure. The residue was extracted with ethyl acetate and the organic layer was washed with saturated NaCl solution, dehydrated over anhydrous sodium sulfate, filtered, and concentrated. The residue was purified by silica gel chromatography (hexane:ethyl acetate=5:1) to provide 2.8 g of (2R, 3S)-3-N,N-dibenzylamino-2-hydroxy-4-phenylbutyric acid methyl ester as colorless oil. Yield 74%. The $^1$H-NMR spectrum of this compound was identical with that of the compound obtained in Example 5. Optical purity: 97%.

EXAMPLE 8

Production of (2R, 3S)-3-N,N-dibenzylamino-2-hydroxy-4-phenylbutyric Acid

In 70 mL of methanol was dissolved 2.85 g (7.3 mmol) of (2R, 3S)-3-N,N-dibenzylamino-2-hydroxy-4-phenylbutyric acid methyl ester, followed by addition of 40 mL of water and 19 mL of 1 N-sodium hydroxide/H$_2$O. The mixture was stirred at room temperature for 48 hours. This reaction mixture was adjusted to pH 2 with 1 N-hydrochloric acid and the methanol was distilled off under reduced pressure. The residue was extracted with ethyl acetate (50 mL×3) and the organic layer was washed with saturated NaCl solution, dehydrated over anhydrous sodium sulfate, and distilled to remove the solvent under reduced pressure. The crude product thus obtained was purified by silica gel chromatography (hexane:ethyl acetate=1:1) to provide 2.3 g of (2R, 3S)-3-N,N-dibenzylamino-2-hydroxy-4-phenylbutyric acid as white solid. Yield: 82%.

$^1$H-NMR (400 MHz, CDCl$_3$) δ: 3.04 (dd, J=3.4, 13.7 Hz, 1H), 3.23 (dd, J=9.7, 13.7 Hz, 1H), 3.37 (ddd, J=2.6, 3.4, 9.7 Hz, 1H), 3.65 (d, J=13.2 Hz, 1H), 3.93 (d, J=2.6 Hz, 1H), 4.45 (d, J=13.2 Hz, 2H), 7.20–7.33 (m, 15H).

EXAMPLE 9

Production of (2R, 3S)-3-amino-2-hydroxy-4-phenylbutyric Acid

In 25 mL of methanol was dissolved 2.05 g (5.5 mmol) of (2R, 3S)-3-N,N-dibenzylamino-2-hydroxy-4-phenylbutyric acid. After the internal atmosphere of the reactor was replaced with argon gas, 500 mg of Pd(OH)$_2$C was added. The reaction system was purged with hydrogen gas and the reaction was carried out in the hydrogen atmosphere at room temperature for 9 hours. The reaction mixture was then filtered with the aid of Celite, washed with 1 N-hydrochloric acid and concentrated under reduced pressure to recover the hydrochloride of (2R, 3S)-3-amino-2-hydroxy-4-phenylbutyric acid. This hydrochloride was dissolved in water and passed through a column packed with ion exchange resin (50 w×4, 100 cc) and washed with water in advance. When the pH of the eluate had become about 5, 10% aqueous ammonia was passed and the eluate was concentrated to give 981 mg of (2R, 3S)-3-amino-2-hydroxy-4-phenylbutyric acid as white crystals. Yield: 92%. The crystals were dissolved in 100 mL of water and the solution was cooled to 5° C. while acetone was gradually added, whereby 413 mg of white crystals were obtained. The mother liquor was concentrated and subjected to the same procedure to give 328 mg of crystals. Optical purity ≧99% ee; chemical purity: 99.6%.

$^1$H-NMR (400 MHz, D$_2$O) δ: 2.95 (dd, J=8.8, 14.2 Hz, 1H), 3.16 (dd, J=6.8, 14.2 Hz, 1H), 3.79 (dd, J=6.8, 8.8 Hz, 1H), 7.36–7.46 (m, 5H).

HPLC conditions: Column: Cosmosil 5C8 (4.6 mm×250 mm); Mobile phase: buffer/methanol=9/1; Buffer: KH$_2$PO$_4$—H$_3$PO$_4$ (pH=2.5); Flow rate: 0.5 ml/min; UV: 210 nm; Temperature: 30° C.; Retention times: 25.7 min (2R, 3S), 16.8 min (2S, 3S); Column: DAICEL CRAWN-PAK CR (4.6 mm×150 mm)×2; Mobile phase: HClO$_4$ (pH=1)/methanol 9/1; Flow rate: 0.4 ml/min; UV: 210 nm; Temperature: 5° C.; Retention times: 54.8 min (2R, 3S), 61.4 min (2S, 3R).

EXAMPLE 10

Production of (3S)-3-N,N-dibenzylamino-2-oxo-4-phenylbutyric Acid Methyl Ester

A solution of (3S)-3-N,N-dibenzylamino-1-methylsulfinyl-2-oxo-4-phenylbutane (810 mg, 2.0 mmol) in tetrahydrofuran (8 mL) was cooled to 0° C., and 80 mg (60%, 2 mmol) of sodium hydride was added. The mixture was stirred for 1 hour and a solution of N-bromosuccinimide (370 mg, 2.1 mmol, 1.05 equivalents) in tetrahydrofuran (4 mL) was added dropwise. After 1 hour, 1 mL of concentrated hydrochloric acid and 20 mL of methanol were added and the mixture was heated to 60° C. and reacted for 10 hours. This reaction mixture was neutralized with an aqueous solution of sodium hydrogencarbonate and the methanol and tetrahydrofuran were distilled off under reduced pressure. The residue was extracted with ethyl acetate (20 mL×3) and the organic layer was washed with saturated NaCl solution, dehydrated over anhydrous sodium sulfate, filtered, and concentrated. The residue was purified by silica gel column chromatography (hexane:ethyl acetate=15:1) to provide 315 mg of (3S)-3-N,N-dibenzylamino-2-oxo-4-phenylbutyric acid methyl ester as light-yellow oil. Yield: 41%. The $^1$H-NMR spectrum of this compound was identical with that of the compound obtained in Example 1.

REFERENCE EXAMPLE

Production of (3S)-3-N,N-dibenzylamino-1-methylsulfinyl-2-oxo-4-phenylbutane

In 70 mL of dimethyl sulfoxide was suspended 6.5 g (60%, 163.2 mmol) of sodium hydride, and the suspension was heated at 70° C. for 60 minutes. To the resulting solution was added 70 mL of tetrahydrofuran, followed by cooling to 0° C., and a solution of N,N-dibenzyl-(L)-phenylalanine benzyl ester (24.0 g, 55.1 mmol) in tetrahydrofuran (50 mL) was added dropwise. After 40 minutes of reaction, the reaction mixture was diluted with 200 mL of 10% citric acid and 200 mL of ethyl acetate for extraction. The organic layer was washed with 100 mL of saturated NaCl solution, dehydrated over anhydrous sodium sulfate, filtered, and concentrated. The residue was purified by silica gel column chromatography (hexane:ethyl acetate=5:1 to 1:1) to provide 19.4 g of light-yellow solid. Yield: 87%. The diastereomer ratio of the compound as determined by $^1$H-NMR was 6:4.

$^1$H-NMR (400 MHz, CDCl$_3$) δ: 2.24 (s, 1.8H), 2.34 (s, 1.2H), 2.96 (dd, J=3.4, 13.2 Hz, 1H), 3.12–3.19 (m, 1H), 3.54–3.76 (m, 4H), 3.84 (d, J=13.7 Hz, 2H), 3.98–4.09 (m, 1H), 7.10–7.38 (m, 15H).

What is claimed is:

1. A process for producing a β-amino-α-hydroxy acid derivative
which comprises treating a γ-amino-β-keto sulfoxide derivative of the formula (1);

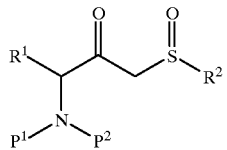

(1)

wherein R$^1$ represents a substituted or unsubstituted alkyl group of 1 to 20 carbon atoms, a substituted or unsubstituted aralkyl group of 7 to 30 carbon atoms or a substituted or unsubstituted aryl group of 6 to 30 carbon atoms; R$^2$ represents a substituted or unsubstituted alkyl group of 1 to 10 carbon atoms, a substituted or unsubstituted aralkyl group of 7 to 20 carbon atoms or a substituted or unsubstituted aryl group of 6 to 20 carbon atoms; P$^1$ and P$^2$ may be the same or different and each represents a substituted or unsubstituted benzyl group, with a halogenating agent to produce a γ-amino-α-halo-β-keto sulfoxide derivative of the formula (2);

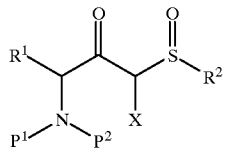

(2)

wherein R$^1$, R$^2$, P$^1$ and P$^2$ are respectively as defined above; X represents a halogen atom, treating the derivative (2) with an acid and an alcohol of the formula (3);

R$^3$OH (3)

wherein R$^3$ represents a substituted or unsubstituted alkyl group of 1 to 10 carbon atoms or a substituted or unsubstituted aralkyl group of 7 to 20 carbon atoms, to produce a β-amino-α-keto ester derivative or β-amino-α-keto acid derivative of the formula (4);

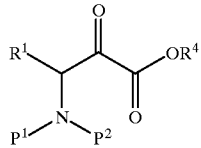

(4)

wherein R$^1$, P$^1$ and P$^2$ are respectively as defined above; R$^4$ represents a hydrogen atom, or a substituted or unsubstituted alkyl group of 1 to 10 carbon atoms or substituted or unsubstituted aralkyl group of 7 to 20 carbon atoms which corresponds to R$^3$ in the above formula (3), and reducing the same derivative (4), optionally followed by cleaving the ester and/or deprotecting the amino group to give a β-amino-α-hydroxy acid derivative of the formula (5);

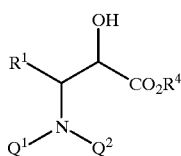

(5)

wherein $R^1$ and $R^4$ are respectively as defined above; $Q^1$ represents a hydrogen atom, or a substituted or unsubstituted benzyl group corresponding to $P^1$ in the above formula (1); $Q^2$ represents a hydrogen atom, or a substituted or unsubstituted benzyl group corresponding to $P^2$ in the above formula (1).

2. A process for producing a β-amino-α-hydroxy acid derivative which comprises treating a γ-amino-β-keto sulfoxide derivative metal salt of the formula (6);

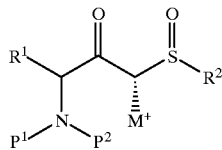

(6)

wherein $R^1$ represents a substituted or unsubstituted alkyl group of 1 to 20 carbon atoms, a substituted or unsubstituted aralkyl group of 7 to 30 carbon atoms or a substituted or unsubstituted aryl group of 6 to 30 carbon atoms; $R^2$ represents a substituted or unsubstituted alkyl group of 1 to 10 carbon atoms, a substituted or unsubstituted aralkyl group of 7 to 20 carbon atoms or a substituted or unsubstituted aryl group of 6 to 20 carbon atoms; $P^1$ and $P^2$ may be the same or different and each represents a substituted or unsubstituted benzyl group; M represents an alkali metal or an alkaline earth metal halide, with a halogenating agent to produce a γ-amino-α-halo-β-keto sulfoxide derivative of the formula (2);

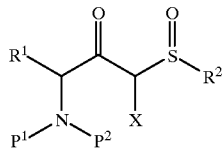

(2)

wherein $R^1$, $R^2$, $P^1$ and $P^2$ are respectively as defined above; X represents a halogen atom, treating the derivative (2) with an acid and an alcohol of the formula (3);

$R^3OH$ (3)

wherein $R^3$ represents a substituted or unsubstituted alkyl group of 1 to 10 carbon atoms or a substituted or unsubstituted aralkyl group of 7 to 20 carbon atoms, to produce a β-amino-α-keto ester derivative or β-amino-α-keto acid derivative of the formula (4);

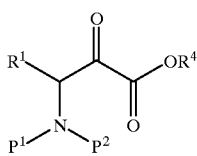

(4)

wherein $R^1$, $P^1$ and $P^2$ are respectively as defined above; $R^4$ represents a hydrogen atom, or a substituted or unsubstituted alkyl group of 1 to 10 carbon atoms or substituted or unsubstituted aralkyl group of 7 to 20 carbon atoms which corresponds to $R^3$ in the above formula (3), and reducing the same derivative (4), optionally followed by cleaving the ester and/or deprotecting the amino group to give a β-amino-α-hydroxy acid derivative of the formula (5);

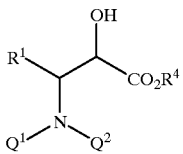

(5)

wherein $R^1$ and $R^4$ are respectively as defined above; $Q^1$ represents a hydrogen atom, or a substituted or unsubstituted benzyl group corresponding to $P^1$ in the above formula (1); $Q^2$ represents a hydrogen atom, or a substituted or unsubstituted benzyl group corresponding to $P^2$ in the above formula (1).

3. The process according to claim 2 wherein the γ-amino-β-keto sulfoxide derivative metal salt of the formula (6) is obtainable by reacting an α-amino acid ester derivative of the formula (7);

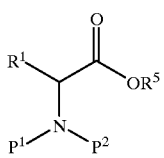

(7)

wherein $R^1$ represents a substituted or unsubstituted alkyl group of 1 to 20 carbon atoms, a substituted or unsubstituted aralkyl group of 7 to 30 carbon atoms or a substituted or unsubstituted aryl group of 6 to 30 carbon atoms; $R^5$ represents a substituted or unsubstituted alkyl group of 1 to 10 carbon atoms, a substituted or unsubstituted aralkyl group of 7 to 20 carbon atoms or a substituted or unsubstituted aryl group of 6 to 20 carbon atoms; $P^1$ and $P^2$ may be the same or different and each represents a substituted or unsubstituted benzyl group, with a sulfoxide metal salt of the formula (8);

$R^2S(=O)CH_2^-M^+$ (8)

wherein $R^2$ represents a substituted or unsubstituted alkyl group of 1 to 10 carbon atoms, a substituted or unsubstituted aralkyl group of 7 to 20 carbon atoms or a substituted or unsubstituted aryl group of 6 to 20 carbon atoms; M represents an alkali metal or an alkaline earth metal halide.

4. The process according to claim 2 wherein the compound of the formula (6) is obtainable by treating, with a base in advance, the compound of the formula (1);

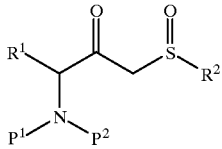
(1)

wherein $R^1$ represents a substituted or unsubstituted alkyl group of 1 to 20 carbon atoms, a substituted or unsubstituted aralkyl group of 7 to 30 carbon atoms or a substituted or unsubstituted aryl group of 6 to 30 carbon atoms; $R^2$ represents a substituted or unsubstituted alkyl group of 1 to 10 carbon atoms, a substituted or unsubstituted aralkyl group of 7 to 20 carbon atoms or a substituted or unsubstituted aryl group of 6 to 20 carbon atoms; $P^1$ and $P^2$ may be the same or different and each represents a substituted or unsubstituted benzyl group.

5. The process according to claim 1, 2, 3 or 4 wherein $R^1$, $P^1$ and $P^2$ each represents a benzyl group.

6. The process according to claim 1, wherein $R^2$ represents a methyl group.

7. The process according to claim 1, wherein the halogenating agent is sulfuryl chloride and X represents a chlorine atom.

8. The process according to claim 1, wherein the halogenating agent is N-bromosuccinimide, 1,3-dibromo-5,5-dimethylhydantoin or bromine and X represents a bromine atom.

9. The process according to claim 8 wherein the halogenating agent is N-bromosuccinimide.

10. The process according to claim 1, wherein $R^3$ represents a methyl group or an ethyl group.

11. The process according to claim 1, wherein $R^4$ is $R^3$.

12. The process according to claim 11 wherein the reduction reaction of the β-amino-α-keto ester derivative of the formula (4), in which $R^4$ is $R^3$, is carried out using a metal hydride.

13. The process according to claim 1, wherein an optically active form of the compound of the formula (1) is used to provide an optically active form of the compound of the formula (5).

14. The process according to claim 1, wherein the reduction reaction is carried out stereoselectively to provide the compound of the formula (5) as a threo isomer.

15. A process for producing a β-amino-α-keto ester derivative or β-amino-α-keto acid derivative which comprises treating a γ-amino-β-keto sulfoxide derivative of the formula (1);

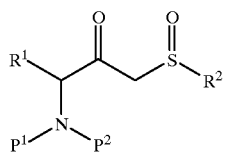
(1)

wherein $R^1$ represents a substituted or unsubstituted alkyl group of 1 to 20 carbon atoms, a substituted or unsubstituted aralkyl group of 7 to 30 carbon atoms or a substituted or unsubstituted aryl group of 6 to 30 carbon atoms; $R^2$ represents a substituted or unsubstituted alkyl group of 1 to 10 carbon atoms, a substituted or unsubstituted aralkyl group of 7 to 20 carbon atoms or a substituted or unsubstituted aryl group of 6 to 20 carbon atoms; $P^1$ and $P^2$ may be the same or different and each represents a substituted or unsubstituted benzyl group, with a halogenating agent to produce a γ-amino-α-halo-β-keto sulfoxide derivative of the formula (2);

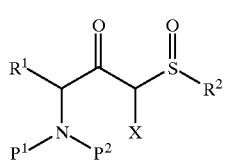
(2)

wherein $R^1$, $R^2$, $P^1$ and $P^2$ are respectively as defined above; X represents a halogen atom, treating the derivative (2) with an acid and an alcohol of the formula (3);

$R^3OH$ (3)

wherein $R^3$ represents a substituted or unsubstituted alkyl group of 1 to 10 carbon atoms or a substituted or unsubstituted aralkyl group of 7 to 20 carbon atoms, to produce a β-amino-α-keto ester derivative or β-amino-α-keto acid derivative of the formula (4);

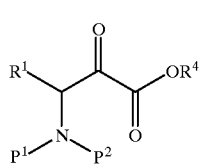
(4)

wherein $R^1$, $P^1$ and $P^2$ are respectively as defined above; $R^4$ represents a hydrogen atom, or a substituted or unsubstituted alkyl group of 1 to 10 carbon atoms or substituted or unsubstituted aralkyl group of 7 to 20 carbon atoms which corresponds to $R^3$ in the above formula (3).

16. A process for producing a β-amino-α-keto ester derivative or β-amino-α-keto acid derivative which comprises treating a γ-amino-β-keto sulfoxide derivative metal salt of the formula (6);

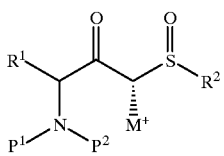

(6)

wherein R¹ represents a substituted or unsubstituted alkyl group of 1 to 20 carbon atoms, a substituted or unsubstituted aralkyl group of 7 to 30 carbon atoms or a substituted or unsubstituted aryl group of 6 to 30 carbon atoms; R² represents a substituted or unsubstituted alkyl group of 1 to 10 carbon atoms, a substituted or unsubstituted aralkyl group of 7 to 20 carbon atoms or a substituted or unsubstituted aryl group of 6 to 20 carbon atoms; P¹ and P² may be the same or different and each represents a substituted or unsubstituted benzyl group; M represents an alkali metal or an alkaline earth metal halide, with a halogenating agent to produce a γ-amino-α-halo-β-keto sulfoxide derivative of the formula (2);

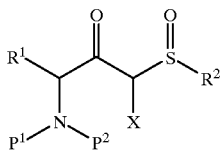

(2)

wherein R¹, R², P¹ and P² are respectively as defined above; X represents a halogen atom, and treating the derivative (2) with an acid and an alcohol of the formula (3);

<p align="center">R³OH (3)</p> wherein R³ represents a substituted or unsubstituted alkyl group of 1 to 10 carbon atoms or a substituted or unsubstituted aralkyl group of 7 to 20 carbon atoms, to produce a β-amino-α-keto ester derivative or β-amino-α-keto acid derivative of the formula (4);

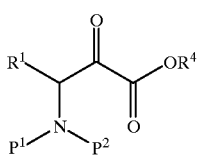

(4)

wherein R¹, P¹ and P² are respectively as defined above; R⁴ represents a hydrogen atom, or a substituted or unsubstituted alkyl group of 1 to 10 carbon atoms or substituted or unsubstituted aralkyl group of 7 to 20 carbon atoms which corresponds to R³ in the above formula (3).

17. The process according to claim 16 wherein the γ-amino-β-keto sulfoxide derivative metal salt of the formula (6) is obtainable by reacting an α-amino acid ester derivative of the formula (7);

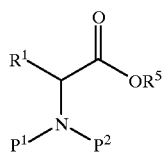

(7)

wherein R¹ represents a substituted or unsubstituted alkyl group of 1 to 20 carbon atoms, a substituted or unsubstituted aralkyl group of 7 to 30 carbon atoms or a substituted or unsubstituted aryl group of 6 to 30 carbon atoms; R⁵ represents a substituted or unsubstituted alkyl group of 1 to 10 carbon atoms, a substituted or unsubstituted aralkyl group of 7 to 20 carbon atoms or a substituted or unsubstituted aryl group of 6 to 20 carbon atoms; P¹ and P² may be the same or different and each represents a substituted or unsubstituted benzyl group, with a sulfoxide metal salt of the formula (8);

<p align="center">R²S(=O)CH₂⁻M⁺ (8)</p> wherein R² represents a substituted or unsubstituted alkyl group of 1 to 10 carbon atoms, a substituted or unsubstituted aralkyl group of 7 to 20 carbon atoms or a substituted or unsubstituted aryl group of 6 to 20 carbon atoms; M represents an alkali metal or an alkaline earth metal halide.

18. The process according to claim 16 wherein the compound of the formula (6) is obtainable by treating, with a base in advance, the compound of the formula (1);

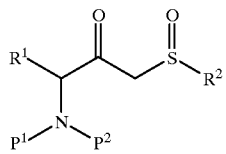

(1)

wherein R¹ represents a substituted or unsubstituted alkyl group of 1 to 20 carbon atoms, a substituted or unsubstituted aralkyl group of 7 to 30 carbon atoms or a substituted or unsubstituted aryl group of 6 to 30 carbon atoms; R² represents a substituted or unsubstituted alkyl group of 1 to 10 carbon atoms, a substituted or unsubstituted aralkyl group of 7 to 20 carbon atoms or a substituted or unsubstituted aryl group of 6 to 20 carbon atoms; P¹ and P² may be the same or different and each represents a substituted or unsubstituted benzyl group.

19. The process according to claim 15, 16, 17 or 18 wherein R¹, P¹ and P² each represents a benzyl group.

20. The process according to claim 15, wherein R² represents a methyl group.

21. The process according to claim 15, wherein the halogenating agent is sulfuryl chloride and X represents a chlorine atom.

22. The process according to claim 15, wherein the halogenating agent is N-bromosuccinimide, 1,3-dibromo-5,5-dimethylhydantoin or bromine and X represents a bromine atom.

23. The process according to claim 22 wherein the halogenating agent is N-bromosuccinimide.

24. The process according to claim 15,
wherein $R^3$ represents a methyl group or an ethyl group.
25. The process according to claim 15,
wherein $R^4$ is $R^3$.
26. The process according to claim 15,
wherein an optically active form of the compound of the formula (1) is used to provide an optically active form of the compound of the formula (4).
27. A process for producing a γ-amino-α-halo-β-keto sulfoxide derivative
which comprises treating a γ-amino-β-keto sulfoxide derivative of the formula (1);

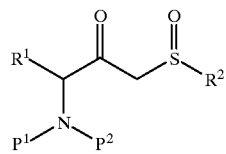

(1)

wherein $R^1$ represents a substituted or unsubstituted alkyl group of 1 to 20 carbon atoms, a substituted or unsubstituted aralkyl group of 7 to 30 carbon atoms or a substituted or unsubstituted aryl group of 6 to 30 carbon atoms; $R^2$ represents a substituted or unsubstituted alkyl group of 1 to 10 carbon atoms, a substituted or unsubstituted aralkyl group of 7 to 20 carbon atoms or a substituted or unsubstituted aryl group of 6 to 20 carbon atoms; $P^1$ and $P^2$ may be the same or different and each represents a substituted or unsubstituted benzyl group, with a halogenating agent to give a γ-amino-α-halo-β-keto sulfoxide derivative of the formula (2);

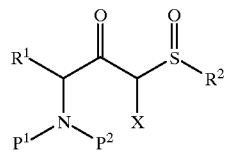

(2)

wherein $R^1$, $R^2$, $P^1$ and $P^2$ are respectively as defined above; X represents a halogen atom.
28. A process for producing a γ-amino-α-halo-β-keto sulfoxide derivative
which comprises treating a γ-amino-β-keto sulfoxide derivative metal salt of the formula (6);

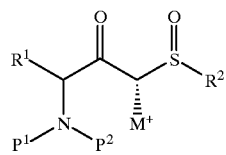

(6)

wherein $R^1$ represents a substituted or unsubstituted alkyl group of 1 to 20 carbon atoms, a substituted or unsubstituted aralkyl group of 7 to 30 carbon atoms or a substituted or unsubstituted aryl group of 6 to 30 carbon atoms; $R^2$ represents a substituted or unsubstituted alkyl group of 1 to 10 carbon atoms, a substituted or unsubstituted aralkyl group of 7 to 20 carbon atoms or a substituted or unsubstituted aryl group of 6 to 20 carbon atoms; $P^1$ and $P^2$ may be the same or different and each represents a substituted or unsubstituted benzyl group; M represents an alkali metal or an alkaline earth metal halide, with a halogenating agent to produce a γ-amino-α-halo-β-keto sulfoxide derivative of the formula (2);

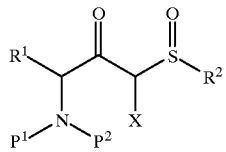

(2)

wherein $R^1$, $R^2$, $P^1$ and $P^2$ are respectively as defined above; X represents a halogen atom.
29. The process according to claim 28
wherein the γ-amino-β-keto sulfoxide derivative metal salt of the formula (6) is obtainable by reacting an α-amino acid ester derivative of the formula (7);

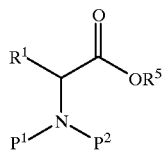

(7)

wherein $R^1$ represents a substituted or unsubstituted alkyl group of 1 to 20 carbon atoms, a substituted or unsubstituted aralkyl group of 7 to 30 carbon atoms or a substituted or unsubstituted aryl group of 6 to 30 carbon atoms; $R^5$ represents a substituted or unsubstituted alkyl group of 1 to 10 carbon atoms, a substituted or unsubstituted aralkyl group of 7 to 20 carbon atoms or a substituted or unsubstituted aryl group of 6 to 20 carbon atoms; $P_1$ and $P^2$ may be the same or different and each represents a substituted or unsubstituted benzyl group, with a sulfoxide metal salt of the formula (8);

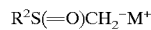

$$R^2S(=O)CH_2^-M^+ \qquad (8)$$

wherein $R^2$ represents a substituted or unsubstituted alkyl group of 1 to 10 carbon atoms, a substituted or unsubstituted aralkyl group of 7 to 20 carbon atoms or a substituted or unsubstituted aryl group of 6 to 20 carbon atoms; M represents an alkali metal or an alkaline earth metal halide.
30. The process according to claim 28
wherein the compound of the formula (6) is obtainable by treating, with a base in advance, the compound of the formula (1);

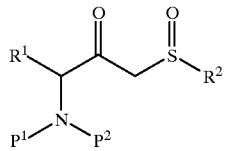

(1)

wherein $R^1$ represents a substituted or unsubstituted alkyl group of 1 to 20 carbon atoms, a substituted or unsubstituted aralkyl group of 7 to 30 carbon atoms or a substituted or unsubstituted aryl group of 6 to 30 carbon atoms; $R^2$ represents a substituted or unsubstituted alkyl group of 1 to 10 carbon atoms, a substituted or unsubstituted aralkyl group of 7 to 20 carbon atoms or a substituted or unsubstituted aryl group of 6 to 20 carbon atoms; $P^1$ and $P^2$ may be the same or different and each represents a substituted or unsubstituted benzyl group.

31. The process according to claim 27, 28, 29 or 30 wherein $R^1$, $P^1$ and $P^2$ each represents a benzyl group.

32. The process according to claim 27, wherein $R^2$ represents a methyl group.

33. The process according to claim 27, wherein the halogenating agent is sulfuryl chloride and X represents a chlorine atom.

34. The process according to claim 27, wherein the halogenating agent is N-bromosuccinimide, 1,3-dibromo-5,5-dimethylhydantoin or bromine and X represents a bromine atom.

35. The process according to claim 34 wherein the halogenating agent is N-bromosuccinimide.

36. A compound of the formula (2);

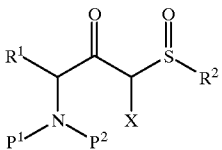

(2)

wherein $R^1$ represents a substituted or unsubstituted alkyl group of 1 to 20 carbon atoms, a substituted or unsubstituted aralkyl group of 7 to 30 carbon atoms or a substituted or unsubstituted aryl group of 6 to 30 carbon atoms; $R^2$ represents a substituted or unsubstituted alkyl group of 1 to 10 carbon atoms, a substituted or unsubstituted aralkyl group of 7 to 20 carbon atoms or a substituted or unsubstituted aryl group of 6 to 20 carbon atoms; $P^1$ and $P^2$ may be the same or different and each represents a substituted or unsubstituted benzyl group; X represents a halogen atom.

37. The compound according to claim 36 wherein $R^1$, $P^1$ and $P^2$ each represents a benzyl group, $R^2$ represents a methyl group, and X represents a chlorine atom or a bromine atom.

38. The compound according to claim 36 or 37 which is optically active.

* * * * *